United States Patent [19]

Best

[11] Patent Number: 5,601,594
[45] Date of Patent: Feb. 11, 1997

[54] NASAL STENT

[76] Inventor: Barry D. Best, 4811 - 1 Croydon Road, Campbell River, British Columbia, Canada, V9H 1C1

[21] Appl. No.: 528,018

[22] Filed: Sep. 14, 1995

[51] Int. Cl.⁶ .................................................. A61M 29/00
[52] U.S. Cl. ............................................. 606/199; 606/196
[58] Field of Search ...................... 606/196, 199; 128/325, 246, 239, 347

[56]     References Cited

U.S. PATENT DOCUMENTS

| 3,903,893 | 9/1975 | Scheer ..................................... 606/196 |
| 3,935,859 | 2/1976 | Doyle . |
| 4,193,396 | 3/1980 | Wacker . |
| 4,293,355 | 10/1981 | Wacker . |
| 4,459,247 | 7/1984 | Rothemund ............................. 128/152 |
| 4,579,112 | 4/1986 | Scott . |
| 4,819,619 | 4/1989 | Augustine et al. ..................... 606/199 |
| 5,044,463 | 9/1991 | Carr . |
| 5,131,411 | 7/1992 | Casali et al. . |
| 5,139,510 | 8/1992 | Goldsmith, III et al. .............. 606/196 |
| 5,188,123 | 2/1993 | Gardner, Jr. . |
| 5,203,352 | 4/1993 | Gardner, Jr. . |
| 5,333,622 | 8/1994 | Casali et al. . |
| 5,336,163 | 8/1994 | DeMane et al. . |
| 5,391,179 | 2/1995 | Mezzoli ................................. 606/196 |

*Primary Examiner*—Michael Powell Buiz
*Assistant Examiner*—Kevin Truong

[57]     ABSTRACT

A nasal stent for packing the nasal cavity following surgery, which includes a deformable cylinder with a breathing passageway therethrough, the cylinder having a diameter slightly larger than that of the nasal cavity of a user at an entranceway into the nasal cavities of the nose, wherein the cylinder has a smooth outer substantially non-absorbent surface that returns to its original shape following deformation.

12 Claims, 1 Drawing Sheet

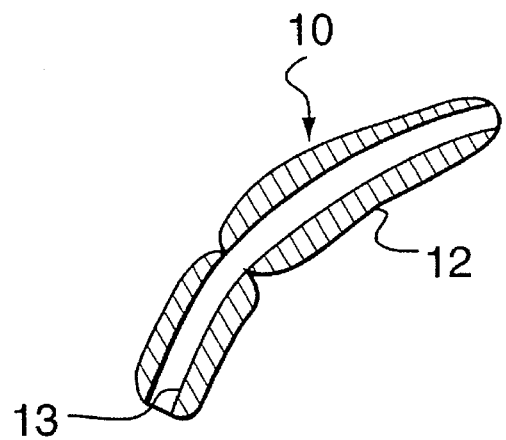
FIG.1
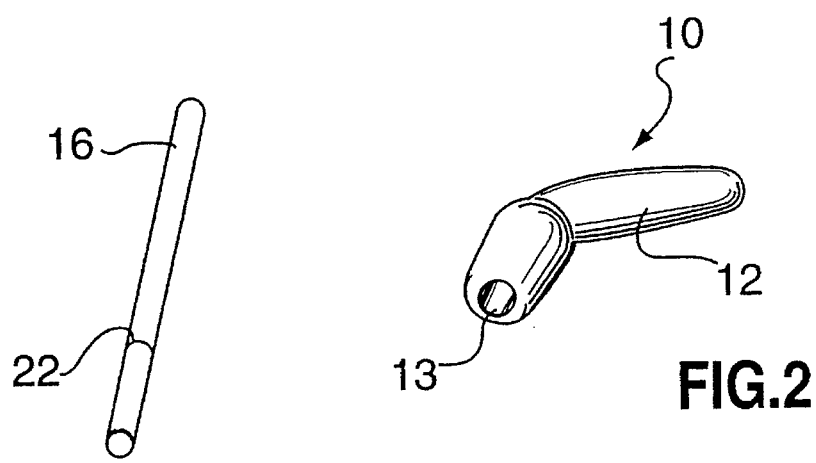
FIG.4
FIG.2
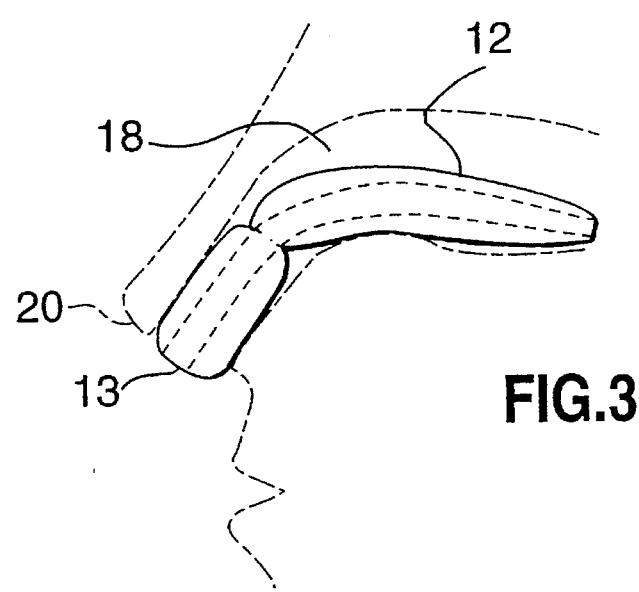
FIG.3

NASAL STENT

FIELD

The present invention relates to a nasal stent which is placed in the nasal passageway following an operation in order to prevent adhesion and scar formation and to create a moist environment in which normal mucosal healing can take place.

BACKGROUND

Following nasal surgery, the lining of the nasal cavity and paranasal sinuses have a tendency to adhere to each other and form scars. Commonly, surgeons pack this cavity with lubricated gauze strips or other materials to prevent adhesions and scars. In some cases a compressed porous material that expands upon contact with fluids is used to prevent nasal hemorrhaging. However, adhesion of the material to the nasal mucosa is often a problem. U.S. Pat. No. 5,336,163 issued to DeMane et al. discloses an expandable nasal stent of highly porous pliable and absorbent foam material having a nonadherent, minimally porous outer surface. DeMane et al. discloses further a groove or hole through the stent that is also minimally absorbent and nonadherent and may also have substantial mechanical strength so as to act as a splint. However, minimizing the porosity on the outer surface also reduces the capacity of the stent to expand and line the mucosal surfaces.

U.S. Pat. No. 3,935,859 issued to Doyle discloses a polyvinyl chloride nasal splint used for nasal surgery with breathing tubes designed to permit breathing. Both tubes are connected together and the web interconnecting the tubes is sutured to the base of the nostril on installation. The material is stated to be flexible. The patent describes the use of gauze saturated with petroleum jelly to form a pad between the septum and the splint plate. The use of gauze and petroleum jelly is an additional step to be taken by the surgeon in putting the splint in place. In addition, the correct amount of gauze must be used to match the size of the nasal passageway and the entire splint with gauze must be replaced periodically once the gauze has become saturated with blood.

It is an object of the invention to provide an improved nasal stent. It is a further object of the invention to provide a nasal stent that is non-absorbent and yet expandable to fill the nasal cavity.

SUMMARY OF THE INVENTION

According to the invention there is provided a nasal stent that is made of a deformable, substantially non-absorbent cylinder having a breathing passageway therethrough with the cylinder having an outer dimension slightly larger than that of the nasal cavity of a user at the entrance-way into the nasal passages. The material of the cylinder can be pre-compressed by rolling a plug of the material between one's hands inserting the material into the nasal passageway and permitting it to expand back to its original dimensions. Such material does not depend upon fluid absorption for its expansion properties, and so exhibits no tendency to adhere to the mucosal lining of the nose. Since it is expandable it can be pre-compressed and then allowed to expand without the necessity of any supplemental pads.

The cylinder material may be a medical grade foam that is substantially non-porous over its outer surface but at the same time soft and resilient. A mixture of polysiloxane with a foaming agent, an expanding agent and a cross-linking agent may be used. The breathing tube may be sufficiently rigid to remain open even when tightly inserted into a nasal cavity.

Advantageously, a elongated, flexible rod may be provided for insertion through said breathing tube to unclog same.

BRIEF DESCRIPTION OF THE DRAWINGS

The novel features believed characteristic of the invention are set forth in the appended claims. The invention itself, however, as well as other features and advantages thereof, will be best understood by reference to the detailed description which follows, read in conjunction with the accompanying drawings, wherein:

FIG. 1 is a sectional view of the nasal stent;

FIG. 2 is a perspective view of the nasal stent;

FIG. 3 shows the nasal stent installed in the nasal cavity of a user; and

FIG. 4 is a perspective view of a plastic rod used to clear the breathing tube of the nasal stent.

DETAILED DESCRIPTION WITH REFERENCE TO THE DRAWINGS

Referring to FIGS. 1 and 2 the nasal stent 10 is made up of a breathing tube 13 enclosed by a contoured, expandable, smooth cylinder 12. Cylinder 12 has smooth outer surfaces and is made of compressible, non-absorbent foam material. The cylinders 12 are made in two sections with the center of the stent 10 having a region of reduced diameter to facilitate bending. The material of cylinders 12 has a smooth, soft, nonporous outer surface to avoid attachment by the mucosal lining of the nose and to bacterial growth in the foam and the creation of conditions conducive to infectious reactions in the nose. Breathing tube 13 is made of a non-absorbent thin plastic material which is sufficiently rigid to avoid collapsing even when tightly packed in a nasal cavity 18.

Referring to FIG. 3 there is shown a simplified drawing of a nasal cavity 18 with the nasal stent 10 inserted. Prior to installation, the nasal stent 10 is rolled between the hands so that its diameter is reduced to the extent that it is smaller than the nasal cavity. Simultaneously, the length of the pads 12 are increased slightly. The nasal stent 10 is inserted to the point that one end is at the entrance-ways 20 to the nasal passageway the nose. The pads 12 expand back to their original diameter which is slightly larger than the size of the nasal cavity 18 at the base 20 of the nose. Thus, a slight pressure is exerted on the mucosal tissue of the nasal cavity 18 with the pads 12 conforming to the shape of the cavity 18 at the base 20.

The absence of any cell structure of the pads 12 and its smooth, outer surface avoids any adherence by the mucosal walls of the nasal cavity 18. The presence of the breathing tube 13 permits the user to breath through the nose and avoid the drying and discomfort caused by breathing through the mouth.

In the event of clogging of the breathing passage the plastic rod 16 may be inserted through the breathing tube 13 and used to clear the passageway thereof. The depth of insertion of the rod 16 can be gauged from the marking which corresponds to insertion up to the end of breathing tube U.S. Pat. No. 4,459,247, which is incorporated herein by reference, describes a method of forming earplugs which involves mixing starting materials of polysiloxane, cross-linking agents, foaming agents and additives, at least one of which is an expanding agent, used to adjust the recovery time and the and the capacity to recover. A suitable mixture is the following:

70 parts by weight dimethylpolysiloxane
30 parts by weight pyrogenic silicic acid
3 parts by weight azodiacarbonamide
1 part by weight diclorobenzoyl peroxide The material is first mixed and preshaped by, for example, extrusion. It is then heated to about 210° C. to give it its final shape and to simultaneously produce cross-linking. Thereafter the cross-linked product is tempered at about 180° C. for a period of 6 hours. The final product has a smooth, soft outer skin free of pores.

Accordingly, while this invention has been described with reference to illustrative embodiments, this description is not intended to be construed in a limiting sense. Various modifications of the illustrative embodiments, as well as other embodiments of the invention, will be apparent to persons skilled in the art upon reference to this description. It is therefore contemplated that the appended claims will cover any such modifications or embodiments as fall within the true scope of the invention.

I claim:

1. A nasal stent for packing the nasal cavity following surgery, comprising:
    a deformable cylinder having a breathing passageway therethrough capable of staying deformed sufficiently long to be inserted into the nasal cavity and having a memory which enables it to return and having a memory which enables it to return to its original shape, said cylinder being of a diameter slightly larger than that of the nasal cavity of a user at an entrance-way into said nasal cavity so that said stent will be held in place by the pressure of walls of said nasal cavity on said cylinder at the entrance-way,
    wherein said cylinder has a smooth outer substantially non-absorbent surface.

2. A nasal stent according to claim 1, wherein said cylinder is a foamed plastic material.

3. A nasal stent according to claim 1, wherein said cylinder is a polysiloxane mixed with an expanding agent and cross-linking agents.

4. A nasal stent according to claim 3, wherein said material is mixed with additives which give it a slow recovery time of between 30 seconds and 2 minutes to recover 90% of its original diameter.

5. A nasal stent according to claim 1, wherein said cylinder is sufficiently rigid so that said passageway remains open even when said cylinder is tightly inserted into a nasal cavity.

6. A nasal stent according to claim 1, including an elongated flexible rod for insertion through said passageway to unclog same.

7. A nasal stent for packing the nasal cavity following surgery, comprising:
    (a) a breathing tube; and,
    (b) a deformable cylinder enclosing said breathing tube, said cylinder capable of staying deformed sufficiently long to be inserted into the nasal cavity and having a memory which enables it to return and having a memory which enables it to return to its original shape;
    said cylinder having said cylinder having a diameter slightly larger than that of the nasal cavity of a user at an entrance-way into said nasal cavity so that said stent will be held in place by the pressure of walls of said nasal cavity on said cylinder at an entrance-way thereto;
    wherein said cylinder has a smooth outer substantially non-absorbent surface.

8. A nasal stent according to claim 7, wherein said material is a foamed plastic with a substantially non-porous, smooth outer surface.

9. A nasal stent according to claim 7, wherein said material is a polysiloxane mixed with expanding and cross-linking agents.

10. A nasal stent according to claim 9, wherein said material is mixed with additives which give it a slow recovery time of between 30 seconds and 2 minutes to recover 90% of its original diameter.

11. A nasal stent according to claim 7, wherein said tube is sufficiently rigid to remain open even when tightly inserted into a nasal cavity.

12. A nasal stent according to claim 7, including an elongated flexible rod for insertion through said breathing tube to unclog same.

* * * * *